United States Patent [19]

Gores

[11] E Re. 28,667

[45] Reissued Dec. 30, 1975

[54] DOUBLE TRAY DENTAL APPARATUS

[75] Inventor: Kenneth W. Gores, Bellevue, Wash.

[73] Assignee: Kirkman Laboratories, Inc., Portland, Oreg.

[22] Filed: Feb. 3, 1972

[21] Appl. No.: 223,343

Related U.S. Patent Documents

Reissue of:

[64] Patent No.: 3,536,069
Issued: Oct. 27, 1970
Appl. No.: 856,395
Filed: Sept. 9, 1969

[52] U.S. Cl. ..... 128/136; 32/14
[51] Int. Cl.² ..... A61F 5/56
[58] Field of Search ..... 32/17, 14; 128/136, 134, 128/260

[56] References Cited

UNITED STATES PATENTS

| | | | |
|---|---|---|---|
| 1,023,213 | 4/1912 | Marcks | 32/17 |
| 2,857,909 | 10/1958 | Johnson | 128/136 |
| 3,416,527 | 12/1968 | Hoef | 128/136 |

*Primary Examiner*—Robert Peshock

[57] ABSTRACT

Apparatus is provided to encase both upper and lower dentition of a human mouth. A pair of trays are resiliently hinged together to apply forces operating in a divergent manner to aid in retention of the apparatus in the mouth during use which may be as a mouthguard and as a medication applicator.

5 Claims, 6 Drawing Figures

INVENTOR
KENNETH W. GORES
BY FORD E. SMITH
ATTORNEY

DOUBLE TRAY DENTAL APPARATUS

Matter enclosed in heavy brackets [ ] appears in the original patent but forms no part of this reissue specification; matter printed in italics indicates the additions made by reissue.

SUMMARY OF THE INVENTION

A feature of this invention has been the provision of two U-shaped trays shaped to encase the upper and lower dentition in the human mouth. Normally the two trays are disposed coplanar in mirrorlike relation. They are joined at the sides by *integral* flexible and resilient hinge means permitting the [troughs] *trays* to be disposed to embrace upper and lower dentition. The hinge means operate to insure seating and retention of the trays in place in the mouth. Spongelike material placed in the tray bottoms provide cushioning and also may serve as a carrier and applicator for oral medication.

DETAILED DESCRIPTION

Figure 1:
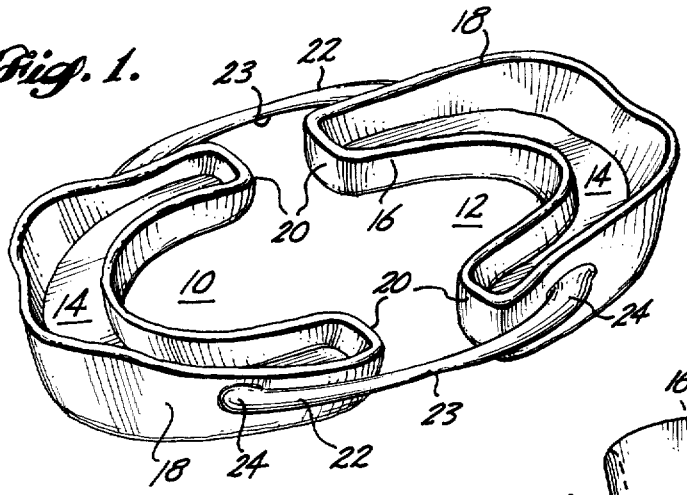
FIG. 1 is a perspective view of the double-tray dental apparatus as it normally appears in coplanar mirrorlike disposition.

Two trays 10 and 12 are arranged in mirrorlike relation to each other as shown in FIG. 1 in which the trays are shown in their normal coplanar disposition. Each tray is U-shaped and comprises a bottom 14, the inner or lingual wall 16. The outer or buccal wall 18 and rear or end walls 20. In the preferred arrangement of trays 10 and 12 the open ends of their U-shapes face each other, as shown.

Hinge members 22,22 span between the trays, being anchored at 24 at their ends *by the lap connections* to like buccal walls 18 of the two trays an appreciable distance forward of the end walls 20.

Desirably the trays 10,12 and hinge members are produced *integrally* by plastic molding techniques from pliant materials of which polyvinyl chloride, polyethylene and similar plastic materials are suitable. For the sake of comfort to the user, the trays should not be hard and inflexible.

Figure 2:
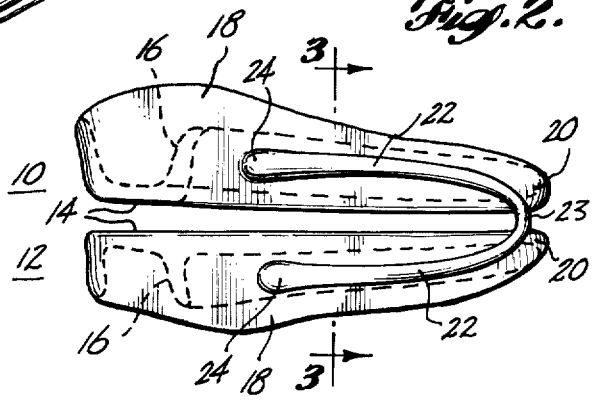
FIG. 2 is a side view of the apparatus disposed to embrace upper and lower dentition.
Figure 3:
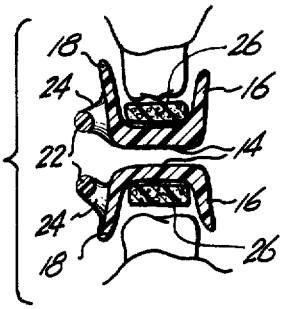
FIG. 3 is a cross-section on line 3—3 of FIG. 2.
Figure 4:
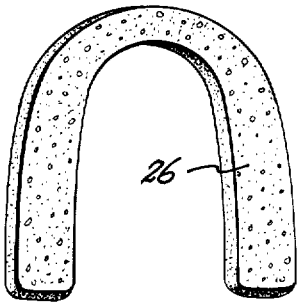
FIG. 4 is a perspective view of a resilient, spongelike single tray insert.

The channel cavity in each tray is configured and sized and shaped to loosely fit either the upper or lower dentition of a user when the apparatus is folded as in FIG. 2. In such situation the flexible hinge members 22 are bent or bowed so that their natural resilience functions to exert divergent forces tending to press and hold the trays into contact with the user's teeth.

The elongate form of hinge members 22 permits the trays to conform to the user's jaws with respect to anterior-posterior as well as lateral malrelationship. In other words, a tray may shift forward and rearward as well as laterally with respect to the other tray to obtain the desired conformance.

While this apparatus may be used as a mouthguard by athletes engaging in body contact sports, it has another valuable use in the application of medicinal compounds. An insert 26 formed of spongelike resilient material may be disposed in the cavity of either or both trays. A particular such use is concerned with applying fluoride compounds which are available in liquid and gel form. Such compound may be introduced to the insert or inserts in place in the apparatus. When the two trays are placed in the mouth, the user bites down and compresses the insert material causing the medication to be forced into all interproximal spaces and around and about the teeth. Relief of such pressure causes a sucking back. The result is a thorough and complete bathing treatment of the user's dentition.

Figure 5:
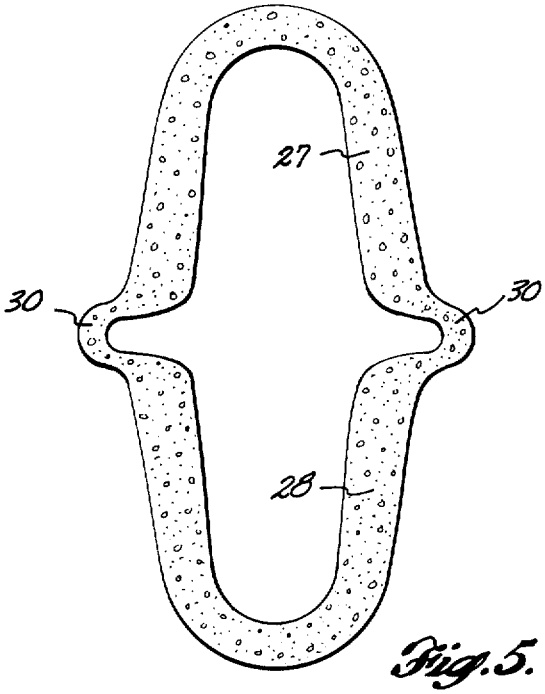
FIG. 5 is a plan view of a double-tray insert.

In FIG. 5 the double insert comprising portions 27,28 are connected by lateral extending bridges 30,30 which also permit lateral and anterior-posterior adjusting movements to accommodate malocclusion.

The bridge members 22 may be medially thinned as at 23 to some degree less than their cross section adjacent their *lap connected and* anchored ends to facilitate the lateral and anterior-posterior shifting required where malocclusion is encountered.

Figure 6:
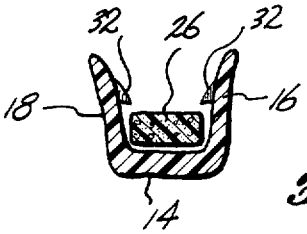
FIG. 6 is a cross section of a tray showing insert retention means.

In FIG. 6 instanding horns 32 are shown on the inner surfaces of the walls 16,18 to overlie the insert 26 to loosely hold it in the channel as the device is being readied or placed in the mouth.

The apparatus here disclosed is the preferred form. It will be apparent to those skilled in the art that alternatives may be employed to accomplish the same results. Also materials may be substituted to obtain equivalent structure and performance.

I claim:

1. Dental apparatus, comprising:

a pair of upper and lower dentition [encasing troughs;] *trays;* a hairpin-shaped resilient bridge member disposed adjacent the buccal exteriors of said paired [troughs] *trays* at each side;

said resilient members each having a U-end between a pair of outwardly biased legs; [and]

*said trays and said resilient members being formed of the same pliant material; and* said legs being joined to said [trough] *tray* sides forward of the posterior portions thereof, *the ends of each said leg having a lap connection, non-pivotally anchoring said end to a tray side, the intermediate portions of said resilient members each having reduced cross-sectional area relative the cross-sections of said leg ends adjacent said lap connections thereby insuring bending of the resilient members into hairpin shape, said lap connections transferring the forces of said resilient members into the tray sides before and behind said connections whereby resilient members in use exert divergent forces on said trays tending to uniformly press and hold the trays into contact with the user's teeth during opening and closing of the jaws and during lateral and anterior/posterior movements thereof.*

2. Apparatus according to claim 1 in which the U-ends of said resilient members are disposed adjacent the posterior portions of said pair [troughs] *of trays* and said legs are attached forward thereof.

[3. Apparatus according to claim 1 in which the troughs and resilient members are formed of pliant material and said resilient members are integrally joined thereto.]

4. Apparatus according to claim 3 in which said [ troughs ] *trays* are closed at their posterior portions.

5. Apparatus according to claim 1 in which porous, spongelike inserts are disposed in said [ troughs. ] *trays*.

6. Apparatus according to claim 5 in which said [ troughs ] *trays* include instanding means upon their inner surfaces to partially overlie and retain said inserts in said [ troughs. ] *trays*.

* * * * *